US009372062B2

(12) United States Patent
Youngner et al.

(10) Patent No.: US 9,372,062 B2
(45) Date of Patent: Jun. 21, 2016

(54) TECHNIQUES FOR CALIBRATING A LINEAR POSITION SENSOR

(71) Applicant: Honeywell International Inc., Morristown, NJ (US)

(72) Inventors: Daniel W. Youngner, Maple Grove, MN (US); Kelly P. Muldoon, Minneapolis, MN (US); Douglas R. Carlson, Woodbury, MN (US)

(73) Assignee: Honeywell International Inc., Morris Plains, NJ (US)

( * ) Notice: Subject to any disclaimer, the term of this patent is extended or adjusted under 35 U.S.C. 154(b) by 398 days.

(21) Appl. No.: 13/886,779

(22) Filed: May 3, 2013

(65) Prior Publication Data

US 2013/0293223 A1 Nov. 7, 2013

Related U.S. Application Data

(60) Provisional application No. 61/642,826, filed on May 4, 2012.

(51) Int. Cl.
| | |
|---|---|
| *G01B 7/14* | (2006.01) |
| *G01D 5/14* | (2006.01) |
| *G01D 18/00* | (2006.01) |
| G01D 5/244 | (2006.01) |
| G01R 33/07 | (2006.01) |
| G01B 7/02 | (2006.01) |
| A61B 5/06 | (2006.01) |
| A61B 19/00 | (2006.01) |

(52) U.S. Cl.
CPC ........ *G01B 7/14* (2013.01); *G01D 5/145* (2013.01); *G01D 18/00* (2013.01); *A61B 5/06* (2013.01); *A61B 2019/5251* (2013.01); *G01B 7/023* (2013.01); *G01D 5/2448* (2013.01); *G01R 33/07* (2013.01)

(58) Field of Classification Search
CPC ....... G01B 7/14; G01D 5/145; G01D 5/2448; A61B 5/06; A61B 2019/5251
USPC ...................................................... 324/207.12
See application file for complete search history.

(56) References Cited

U.S. PATENT DOCUMENTS

| | | | | | |
|---|---|---|---|---|---|
| 4,970,464 | A | * | 11/1990 | Williams | ................. 324/207.13 |
| 5,568,048 | A | * | 10/1996 | Schroeder et al. | ....... 324/207.21 |
| 5,608,317 | A | * | 3/1997 | Hollmann | .................. 324/207.2 |
| 5,865,769 | A | * | 2/1999 | Case et al. | .................... 600/587 |

(Continued)

*Primary Examiner* — Jermele M Hollington
*Assistant Examiner* — Christopher McAndrew
(74) *Attorney, Agent, or Firm* — Conley Rose, P.C.; Kristin Jordan Harkins

(57) ABSTRACT

Techniques are described for sensing a position of an object located within an enclosure over a position range. The techniques include generating an expected output signal of each of a plurality of magnetic field sensors disposed along an outer surface of the enclosure, receiving actual output signals from the sensors, wherein each actual output signal indicates a relative proximity of a magnetic target coupled to the object to the corresponding sensor. The techniques further include superimposing the expected output signal over the actual output signals, and iteratively shifting the expected output signal over position relative to the actual output signals and comparing the shifted expected output signal to the actual output signals, until the expected output signal compared to the actual output signals corresponds to a substantially minimized error parameter. The position of the object may then be determined based at least in part on the shifted expected output signal.

20 Claims, 8 Drawing Sheets

(56) References Cited

U.S. PATENT DOCUMENTS

| | | | |
|---|---|---|---|
| 5,952,823 A * | 9/1999 | Nyce et al. | 324/207.13 |
| 5,955,881 A * | 9/1999 | White et al. | 324/207.2 |
| 6,190,319 B1 * | 2/2001 | Goldowsky | 600/437 |
| 6,208,133 B1 * | 3/2001 | Ehling et al. | 324/202 |
| 6,307,365 B1 * | 10/2001 | Santos et al. | 324/207.12 |
| 7,064,559 B2 * | 6/2006 | Bissonnette et al. | 324/662 |
| 2010/0198569 A1 * | 8/2010 | Wu et al. | 703/6 |
| 2013/0066587 A1 * | 3/2013 | Kalathil et al. | 702/150 |

\* cited by examiner

TECHNIQUES FOR CALIBRATING A LINEAR POSITION SENSOR

CROSS-REFERENCE TO RELATED APPLICATIONS

This application claims the benefit of U.S. Provisional Application No. 61/642,826, entitled "TECHNIQUES FOR CALIBRATING A LINEAR POSITION SENSOR" and filed May 4, 2012, the entire content of which is incorporated by reference herein.

TECHNICAL FIELD

This disclosure relates to position sensors, and more particularly, to techniques for calibrating a position sensor.

BACKGROUND

Position sensors are among a number of electro-mechanical transducers that may be used to sense a position of an object. For example, position sensors may be configured to sense an actual, or "absolute," position of an object, as well as a "relative" position, or a displacement, of the object. In some cases, position sensors may be referred to as position "encoders." A particular position sensor may comprise any of a wide variety of linear and angular, or "rotary," position sensors. In some examples, position sensors may use contact-based sensing means to sense a position of an object by mechanically coupling the object to the position sensor, e.g., to a movable member or a rotating shaft of the position sensor, which may be mechanically coupled to a sensing element of the position sensor. In other examples, position sensors may employ a wide variety of contactless sensing means, such as optical, magnetic, capacitive, and inductive sensing means, as some examples. Position sensors employing such contactless sensing means may be less susceptible to wear and may provide greater durability compared to contact-based position sensors.

For example, a linear position sensor, or "encoder," may be configured to sense a position of an object moving along a linear trajectory relative to the linear position sensor. As one example, the linear position sensor may sense a position of an encoder "read-head" that is coupled to the object relative to an encoder track as the encoder read-head and the object move together along the encoder track. The position of the read-head relative to the encoder track may be sensed using mechanical, optical, magnetic, capacitive, or inductive sensing means, as well as other sensing means. As another example, in the case of a linear position sensor employing magnetic sensing means as described above, the linear position sensor may sense a position of a magnetic target that is coupled to the object relative to one or more magnetic field sensors disposed along a base of the linear position sensor. In this example, the magnetic target may be configured to generate a uniform magnetic field that varies relative to the one or more magnetic field sensors based on the position of the magnetic target, and therefore the object, relative to the sensors. Accordingly, the one or more magnetic field sensors may be configured to sense the magnetic field as the magnetic target and the object move together along the base. For example, the one or more magnetic field sensors may include magnetoresistive (MR) sensors, including anisotropic magnetoresistive (AMR) sensors, Hall effect sensors, or other magnetic sensors.

SUMMARY

In general, this disclosure describes techniques for calibrating a position sensor used to sense a position of an object located within an enclosure over a position range. The techniques described herein may, in some cases, enable accurately sensing the position of the object located within the enclosure over the position range using magnetic sensing means, in particular, in applications where the enclosure attenuates or otherwise distorts a magnetic field passing through the enclosure. In some examples, the position range may comprise a substantially linear position range. However, the techniques of this disclosure may be equally applicable to other position sensors, including position sensors configured to sense a position of an object located within an enclosure over a non-linear position range (e.g., a substantially angular, or a partially angular position range).

In one example, a method of sensing a position of an object located within an enclosure over a position range includes generating an expected output signal of each of a plurality of magnetic field sensors disposed along an outer surface of the enclosure between a first end and a second end of the enclosure; receiving a plurality of actual output signals from the plurality of magnetic field sensors, wherein each of the plurality of actual output signals indicates a relative proximity of a magnetic target coupled to the object to the corresponding one of the plurality of magnetic field sensors; superimposing the expected output signal over the plurality of actual output signals; iteratively shifting the expected output signal over position relative to the plurality of actual output signals and comparing the shifted expected output signal to the plurality of actual output signals, until the shifted expected output signal compared to the plurality of actual output signals corresponds to a substantially minimized error parameter; and determining the position of the object within the enclosure over the position range based at least in part on the shifted expected output signal.

In another example, a device for sensing a position of an object located within an enclosure over a position range includes means for generating an expected output signal of each of a plurality of magnetic field sensors disposed along an outer surface of the enclosure between a first end and a second end of the enclosure; means for receiving a plurality of actual output signals from the plurality of magnetic field sensors, wherein each of the plurality of actual output signals indicates a relative proximity of a magnetic target coupled to the object to the corresponding one of the plurality of magnetic field sensors; means for superimposing the expected output signal over the plurality of actual output signals; means for iteratively shifting the expected output signal over position relative to the plurality of actual output signals and comparing the shifted expected output signal to the plurality of actual output signals, until the shifted expected output signal compared to the plurality of actual output signals corresponds to a substantially minimized error parameter; and means for determining the position of the object within the enclosure over the position range based at least in part on the shifted expected output signal.

In another example, an apparatus for sensing a position of an object located within an enclosure over a position range is configured to generate an expected output signal of each of a plurality of magnetic field sensors disposed along an outer surface of the enclosure between a first end and a second end of the enclosure; receive a plurality of actual output signals from the plurality of magnetic field sensors, wherein each of the plurality of actual output signals indicates a relative proximity of a magnetic target coupled to the object to the corresponding one of the plurality of magnetic field sensors; superimpose the expected output signal over the plurality of actual output signals; iteratively shift the expected output signal over position relative to the plurality of actual output signals and comparing the shifted expected output signal to the plurality of actual output signals, until the shifted expected output signal compared to the plurality of actual output signals corresponds to a substantially minimized error parameter; and determine the position of the object within the enclosure over the position range based at least in part on the shifted expected output signal.

The details of one or more examples are set forth in the accompanying drawings and the description below. Other features, objects, and advantages in addition to those described below will be apparent from the description and drawings, and from the claims.

DETAILED DESCRIPTION

Figure 1:
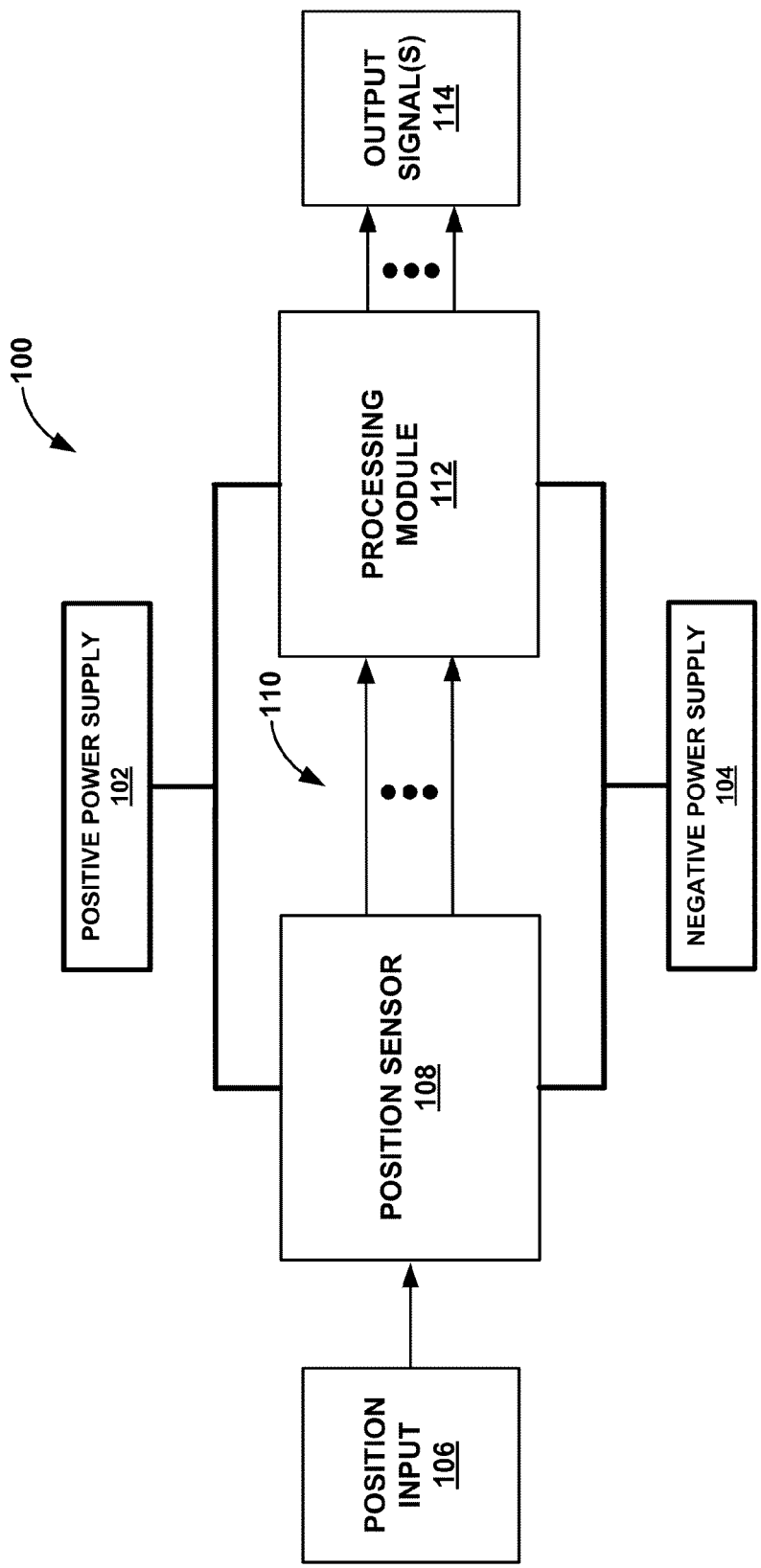
FIG. 1 is a block diagram that illustrates one example of a position sensor calibration system, consistent with the techniques of this disclosure.

In general, this disclosure describes techniques for calibrating a position sensor used to sense a position of an object located within an enclosure over a position range. The techniques described herein may, in some cases, enable accurately sensing the position of the object located within the enclosure over the position range using magnetic sensing means, in particular, in applications where the enclosure attenuates or otherwise distorts a magnetic field passing through the enclosure. In some examples, the position range may comprise a substantially linear position range. However, the techniques of this disclosure may be equally applicable to other position sensors, including position sensors configured to sense a position of an object located within an enclosure over a non-linear position range (e.g., a substantially angular, or a partially angular position range).

Position sensors are among a number of electro-mechanical transducers that may be used to sense a position of an object. For example, position sensors may be configured to sense an actual, or "absolute," position of an object, as well as a "relative" position, or a displacement, of the object. In some cases, position sensors may be referred to as position "encoders." A particular position sensor may comprise any of a wide variety of linear and angular, or "rotary," position sensors. In some examples, position sensors may use contact-based sensing means to sense a position of an object by mechanically coupling the object to the position sensor, e.g., to a movable member or a rotating shaft of the position sensor, which may be mechanically coupled to a sensing element of the position sensor. In other examples, position sensors may employ a wide variety of contactless sensing means, such as optical, magnetic, capacitive, and inductive sensing means, as some examples. Position sensors employing such contactless sensing means may be less susceptible to wear and may provide greater durability compared to contact-based position sensors.

For example, a linear position sensor, or "encoder," may be configured to sense a position of an object moving along a linear trajectory relative to the linear position sensor. As one example, the linear position sensor may sense a position of an encoder "read-head" that is coupled to the object relative to an encoder track as the encoder read-head and the object move together along the encoder track. The position of the read-head relative to the encoder track may be sensed using mechanical, optical, magnetic, capacitive, or inductive sensing means, as well as other sensing means. As another example, in the case of a linear position sensor employing magnetic sensing means as described above, the linear position sensor may sense a position of a magnetic target that is coupled to the object relative to one or more magnetic field sensors disposed along a base of the linear position sensor. In this example, the magnetic target may be configured to generate a uniform magnetic field which varies from the perspective of the one or more magnetic field sensors based on the position of the magnetic target, and therefore the object, relative to the sensors. Accordingly, the one or more magnetic field sensors may be configured to sense the magnetic field as the magnetic target and the object move together along the base. For example, the one or more magnetic field sensors may include magnetoresistive (MR) sensors, including anisotropic magnetoresistive (AMR) sensors, Hall effect sensors, or other magnetic sensors.

Existing position sensors employing the magnetic sensing techniques described above are generally configured to sense a position of a magnetic target that is located within close proximity to a particular position sensor, i.e., to one or more magnetic field sensors of the positions sensor. For example, the position sensor may be configured to sense the position of the magnetic target, wherein the magnetic target is separated from the one or more magnetic field sensors by a small air gap, or by another medium that does not significantly attenuate or otherwise distort a magnetic field generated by the magnetic target. In other words, existing position sensors employing magnetic sensing techniques are generally configured to sense a position of a magnetic target through materials that do not substantially change a magnetic field generated by the magnetic target.

Development of the techniques of this disclosure has demonstrated that position sensors employing magnetic sensing means, as described above, may be used in applications requiring sensing a position of an object located within an enclosure over a position range, and, in particular, in applications where the enclosure possesses any of a wide variety of magnetic field altering properties. Such properties of the enclosure may include, e.g., magnetic field attenuation, hysteresis (or magnetic "memory"), or other properties capable of substantially attenuating or distorting (e.g., interfering with) a magnetic field passing through the enclosure. As one example, the enclosure may comprise a metallic hydraulic cylinder. Without compensating for these adverse properties of the enclosure, for example, using the position sensor calibration techniques described herein, a magnetic field passing through the enclosure and sensed by the position sensor may be substantially altered, which may result in inaccurate position measurement.

Accordingly, the techniques of this disclosure may, in some cases, enable accurately sensing the position of the object located within the enclosure over the position range using magnetic sensing means, for example, in applications where the enclosure attenuates or otherwise distorts a magnetic field passing through the enclosure. Specifically, the techniques may enable calibrating the position sensor such that the position sensor may be used to accurately sense the position of the object within the enclosure, while requiring minimal additional structural and functional hardware and components, and signal processing resources, compared to existing position sensors and related techniques.

FIG. 1 is a block diagram that illustrates one example of a position sensor calibration system 100, consistent with the techniques of this disclosure. As shown in FIG. 1, system 100 includes a positive power supply 102, a negative power supply 104, a position input 106, a position sensor 108, one or more position sensor output signal(s) 110, a processing module 112, and one or more processing module output signal(s) 114. System 100 may comprise an electro-mechanical system or device of any kind, including any combination of mechanical structural components and hardware, electro-mechanical transducers, discrete electronic components, digital and/or analog circuitry, and mechanical and electronic sub-systems or sub-devices of any kind. Examples of processing module 112 are described in greater detail below. Examples of position sensor 108 are also described in greater detail below, as well as with reference to position sensors 200 and 230 of FIGS. 2A and 2B.

In the example of FIG. 1, position input 106 may comprise a position (e.g., a linear position, or an angular position) of an object (not shown) located within an enclosure (also not shown) over a position range (e.g., a linear position range, or an angular position range). In other words, position input 106 may represent a physical position of the object located within the enclosure over the position range. For example, position sensor 108 may be coupled to the enclosure, such that the position range may correspond to a position sensing range of position sensor 108. As an example, the position sensing range of position sensor 108 may comprise a linear position sensing range expressed in units of length, an angular position sensing range expressed in degrees (or radians), or any combination thereof.

It should be noted that, in some examples, processing module 112 may not be included within system 100. In these examples, any functionality attributed to processing module 112 as described herein may be included within position sensor 108. As such, in these examples, an output of system 100 may directly comprise position sensor output signal(s) 110. In other words, position sensor output signal(s) 110 may be directly indicative of the position of the object located within the enclosure over the position range. In other cases, as shown in the example of FIG. 1, the output of system 100 may comprise processing module output signal(s) 114. In these cases, position sensor output signal(s) 110 of position sensor 108 may comprise raw sensor data, and processing module output signal(s) 114 of processing module 112 may comprise the raw sensor data that is further processed to generate signals indicative of the position of the object located within the enclosure over the position range.

In various examples, system 100, and in particular, position sensor 108 and/or processing module 112, may be configured to convert position input 106 from the position of the object (e.g., a linear, or an angular position of the object) located within the enclosure over the position range (e.g., a linear or an angular position range) to one or more electrical signals in order to generate processing module output signal(s) 114 (or, in examples where processing module 112 is not included within system 100, position sensor output signal(s) 110). As described herein, position sensor 108, alone, or in conjunction with processing module 112, may also perform a calibration algorithm consistent with the techniques of this disclosure, as part of generating processing module output signal(s) 114 (or position sensor output signal(s) 110 when processing module 112 is not included within system 100).

In particular, as previously described, performing the calibration algorithm according to the techniques described herein may enable position sensor 108 and/or processing module 112, and system 100 generally, to accurately sense the position of the object located within the enclosure over the position range, e.g., when the enclosure comprises a metallic enclosure, or an enclosure made of another material, such that the enclosure attenuates magnetic fields passing through the enclosure. Furthermore, one or more of positions sensor 108 and processing module 112 may perform additional processing of one or more of position sensor output signal(s) 110 and processing module output signal(s) 114, such as, e.g., filtering, scaling, normalizing, level-shifting, etc.

Each of position sensor 108 and processing module 112 may comprise any suitable arrangement of hardware, software, firmware, or any combination thereof, to perform the techniques attributed to position sensor 108 and processing module 112 in this disclosure. In general, position sensor 108 and processing module 112 may include any of one or more microprocessors, microcontrollers, digital signal processors (DSPs), application specific integrated circuits (ASICs), field programmable gate arrays (FPGAs), or any other equivalent integrated or discrete logic circuitry, as well as any combination of such components. Furthermore, each of position sensor 108 and processing module 112 may include various types of analog circuitry, in addition to, or in place of, the logic devices and circuitry described above.

Additionally, positive power supply 102 and negative power supply 104 may each comprise any power supply unit, module, or circuitry also included within system 100, which may, in some examples, be integrated with position sensor 108 and/or processing module 112 within a common enclosure, or on a common printed circuit board (PCB). Although positive power supply 102, negative power supply 104, position input 106, position sensor 108, position sensor output signal(s) 110, processing module 112, and processing module output signal(s) 114 of system 100 are described as separate units or modules for conceptual purposes, in some examples, any combination of these components of system 100 may be functionally integrated within a common enclosure or housing.

Furthermore, in this disclosure, any reference made to a memory, or a memory device, used to store instructions, data, or other information, includes any volatile or non-volatile media, such as random access memory (RAM), read only memory (ROM), non-volatile RAM (NVRAM), electrically erasable programmable ROM (EEPROM), flash memory, and the like. In some examples, one or more memory devices may be external to system 100, position sensor 108, and/or processing module 112, for example, external to an enclosure or a common PCB used to enclose or house system 100, position sensor 108, and/or processing module 112. In other examples, the one or more memory devices may be internal to system 100, position sensor 108, and/or processing module 112, e.g., included within a common enclosure or on a common PCB.

According to the techniques of this disclosure, as one example, system 100, including position sensor 108 and processing module 112, may be configured to sense a position of an object located within an enclosure over a position range (e.g., a linear, or an angular position range). For example, one or more of position sensor 108 and processing module 112 may be configured to generate an expected output signal of each of a plurality of magnetic field sensors disposed along an outer surface of the enclosure between a first end and a second end of the enclosure. The one or more of position sensor 108 and processing module 112 may be further configured to receive a plurality of actual output signals from the plurality of magnetic field sensors. In this example, each of the plurality of actual output signals may indicate a relative proximity of a magnetic target coupled to the object to the corresponding one of the plurality of magnetic field sensors.

Additionally, the one or more of position sensor 108 and processing module 112 may also be configured to superimpose the expected output signal over the plurality of actual output signals, and iteratively shift the expected output signal over position relative to the plurality of actual output signals and compare the shifted expected output signal to the plurality of actual output signals, until the shifted expected output signal compared to the plurality of actual output signals corresponds to a substantially minimized error parameter. Finally, the one or more of position sensor 108 and processing module 112 may be further configured to determine the position of the object within the enclosure over the position range based at least in part on the shifted expected output signal.

In this manner, position sensor calibration system 100 of FIG. 1 represents an example of a position sensor calibration system configured to perform a method of sensing a position of an object located within an enclosure over a position range, wherein the method performed by the position sensor calibration system comprises generating an expected output signal of each of a plurality of magnetic field sensors disposed along an outer surface of the enclosure between a first end and a second end of the enclosure, receiving a plurality of actual output signals from the plurality of magnetic field sensors, wherein each of the plurality of actual output signals indicates a relative proximity of a magnetic target coupled to the object to the corresponding one of the plurality of magnetic field sensors, superimposing the expected output signal over the plurality of actual output signals, iteratively shifting the expected output signal over position relative to the plurality of actual output signals and comparing the shifted expected output signal to the plurality of actual output signals, until the shifted expected output signal compared to the plurality of actual output signals corresponds to a substantially minimized error parameter, and determining the position of the object within the enclosure over the position range based at least in part on the shifted expected output signal.

Figure 2A:
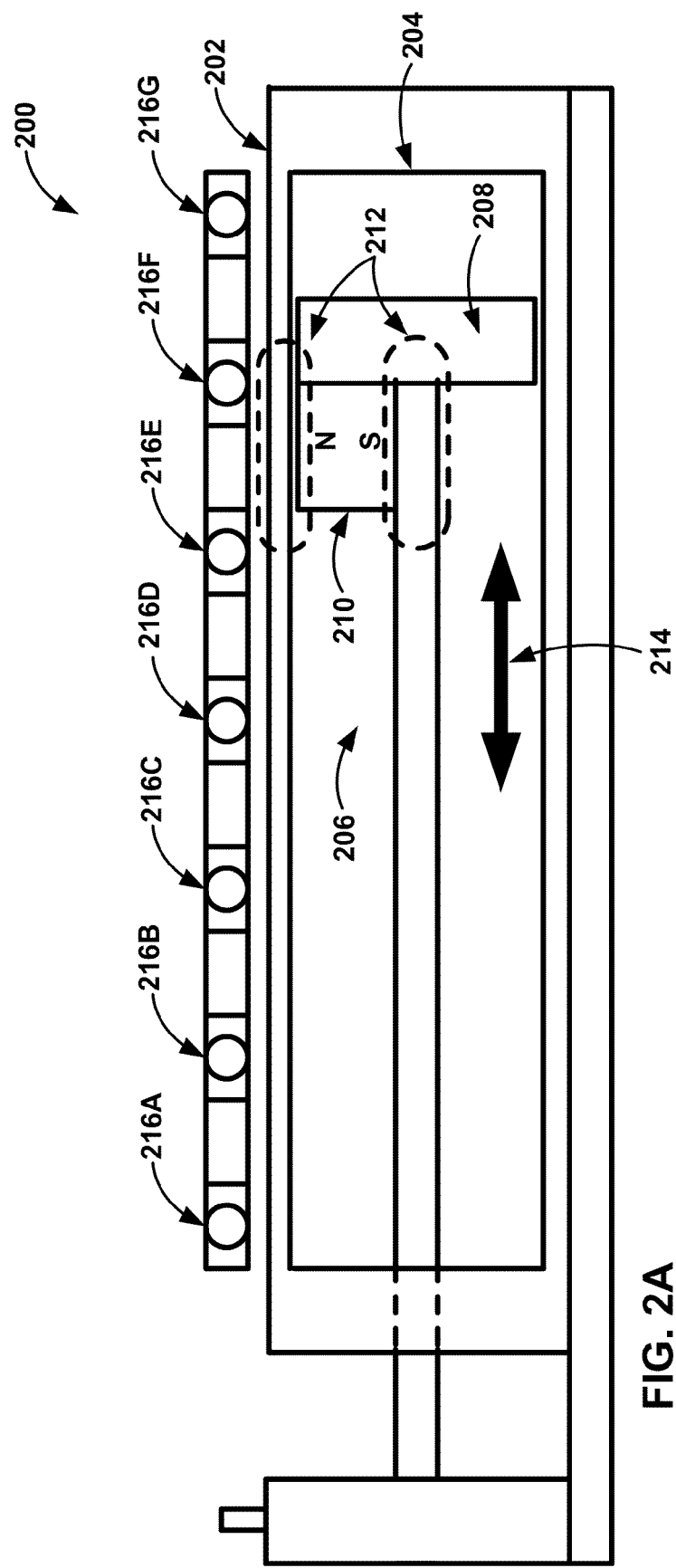
FIGS. 2A and 2B are conceptual diagrams that each illustrate a side view of an example of a linear position sensor that may be used in conjunction with the example position sensor calibration system of FIG. 1, consistent with the techniques of this disclosure.

FIG. 2A is a conceptual diagram that illustrates a side view of one example of a linear position sensor which may be used in conjunction with the example position sensor calibration system of FIG. 1, consistent with the techniques of this disclosure. In other words, position sensor 200 represents one example of position sensor 108 depicted in FIG. 1.

As shown in the example of FIG. 2A, position sensor 200 is implemented as part of a hydraulic cylinder 202 (a cross-sectional view of which is provided in FIG. 2A), which includes, in part, an enclosure 204, a movable piston 206 disposed within enclosure 204 so as to move in a direction 214 (i.e., a left-to-right direction with reference to hydraulic cylinder 202), and a portion of piston 206, which, in this example, may be referred to as the object 208. In the example of FIG. 2A, position sensor 200 may be configured to sense a position of object 208 located within enclosure 204 over a position range. For example, the position range may be defined by the dimensions of enclosure 204, e.g., by a first end and a second end of enclosure 204. In some examples, the position range may be defined by the inner dimensions of enclosure 204. In various examples, in a similar manner as previously described, enclosure 204 of hydraulic cylinder 202 may comprise a metallic enclosure, or an enclosure made of another material, such that enclosure 204 attenuates magnetic fields passing through enclosure 204.

As also shown in FIG. 2A, position sensor 200 also includes a plurality of magnetic field sensors 216A-216G disposed along an outer surface, in this case a top surface, of enclosure 204, between the first and second ends of enclosure 204. In the example of FIG. 2A, the first and second ends of enclosure 204 may be defined by positions of magnetic field sensors 216A and 216G, respectively. In other examples, magnetic field sensors 216A-216G may be disposed along another surface of enclosure 204. Additionally, position sensor 200 also includes a magnetic target 210 also disposed within enclosure 204, that is coupled to object 208. In other examples, magnetic target 210 may be disposed within object 208 (e.g., inside one or more cavities within object 208). As shown in FIG. 2A, magnetic target 210 may include one or more first magnetic poles (e.g., one or more North (N) poles) and one or more second magnetic poles (e.g., one or more South (S) poles) disposed on opposite ends of magnetic target 210 so as to generate a uniform magnetic field 212. In various examples, magnetic target 210 may be configured such that the one or more first (N) magnetic poles and the one or more second (S) magnetic poles are arranged in any orientation, e.g., vertically, horizontally, or otherwise, within enclosure 204.

In the example of FIG. 2A, as object 208, and, therefore, magnetic target 210, move in direction 214 relative to hydraulic cylinder 202, magnetic field sensors 216A-216G may be configured to sense magnetic field 212 generated by magnetic target 210. For example, magnetic field sensors 216A-216E may be configured to sense relative proximity of magnetic target 210 coupled to object 208 to the corresponding one of magnetic field sensors 216A-216G. In this example, each of magnetic field sensors 216A-216G may be configured to generate an output signal in response to uniform magnetic field 212 generated by magnetic target 210, such that each of the output signals generated by magnetic field sensors 216A-216G indicates a relative proximity of magnetic target 210, and therefore of object 208, to the corresponding one of magnetic field sensors 216A-216G.

For example, magnetic field sensors 216A-216G may be configured as an array of magnetic field sensors (e.g., arranged on a common printed circuit board (PCB) substrate), which may be coupled to hydraulic cylinder 202, and, specifically, to the outer surface of enclosure 204, using another enclosure (not shown). This additional enclosure used to couple magnetic field sensors 216A-216G to enclosure 204 also may comprise a metallic enclosure, or an enclosure made of another material, such that the additional enclosure substantially attenuates, or completely shields magnetic fields passing through all surfaces of the additional enclosure other than the surface adjoining enclosure 204. For example, the additional disclosure may comprise a half-cylinder mounted over the top surface of enclosure 204 and containing therein magnetic field sensors 216A-216G. In this manner, each of magnetic field sensors 216A-216G may be configured to generate the corresponding output signal in response to uniform magnetic field 212 generated by magnetic target 210, as described above, while being substantially isolated, or shielded from any external magnetic fields (e.g., any stray magnetic fields) other than uniform magnetic field 212. This isolation or shielding may, in some cases, reduce or prevent interference with the output signals generated by magnetic field sensors 216A-216G by the external magnetic fields.

In the example of FIG. 2A, position sensor 200, including magnetic field sensors 216A-216G, magnetic target 210, hydraulic cylinder 202, and any components thereof may comprise part of an enclosure or housing of position sensor 200. Furthermore, position sensor 200 may be configured to be mounted, via hydraulic cylinder 202, or enclosure 204, within another structure, such as a system (e.g., system 100 of FIG. 1) enclosure or housing, or a system chassis. In some examples, hydraulic cylinder 202 and/or enclosure 204 may further include one or more mounting holes or couplings (not shown), which may be used to mount hydraulic cylinder 202 and/or enclosure 204 within the structure or chassis.

Additionally, magnetic field sensors 216A-216G may be substantially uniformly, or "symmetrically," spaced along the outer surface of enclosure 204 between the first and second ends of enclosure 204, which have been previously described. Alternatively, magnetic field sensors 216A-216G may be non-uniformly, or otherwise asymmetrically, spaced along the outer surface between the first and second ends.

Moreover, consistent with the techniques of this disclosure, one or more of magnetic field sensors 216A-216G may comprise one or more magnetoresistive sensors, including one or more MR and/or AMR sensors. A magnetoresistive sensor, generally, may be configured to sense a magnitude of an external magnetic field applied to the sensor (e.g., until a point of saturation of the sensor), as well as an angle of the external magnetic field relative to the sensor. For example, the sensor may comprise one or more magnetoresistive elements a resistance of each of which may change in response to the angle (and, until the point of saturation, the magnitude) of the external magnetic field relative to the respective magnetoresistive element. For example, the change in resistance of each magnetoresistive element may be proportional to a difference between a direction of a bias current flowing through the element, and an angle of magnetization (which may be referred to as a magnetization vector) of the element by the external magnetic field. In this example, the angle of magnetization of the element by the external magnetic field may be a function of the angle at which the external magnetic field is applied relative to the element.

According to the techniques of this disclosure, in one example, position sensor 200 may be included within a position sensor calibration system (e.g., system 100 of FIG. 1) used to sense a position of object 208 located within enclosure 204 over a position range (e.g., a linear position range defined by the first and second ends of enclosure 204). In this example, position sensor 200 and/or another component of the position sensor calibration system may be configured to generate an expected output signal of each of magnetic field sensors 216A-216G disposed along the outer surface of enclosure 204 between the first end and the second end of enclosure 204. For example, the expected output signal may comprise a signal that is expected to be output by each of magnetic field sensors 216A-216G as magnetic target 210 passes the respective one of magnetic field sensors 216A-216G.

In some examples, to generate the expected output signal, position sensor 200 and/or the other component of the system may be configured to receive a plurality of calibration output signals from magnetic field sensors 216A-216G, wherein each of the plurality of calibration output signals indicates a relative proximity of magnetic target 210 to the corresponding one of magnetic field sensors 216A-216G. Furthermore, position sensor 200 and/or the other component of the system may be configured to normalize the plurality of calibration output signals such that each of the plurality of calibration output signals comprises a substantially same dynamic range, shift the normalized plurality of calibration output signals over position such that the signals of the normalized plurality of calibration output signals are substantially aligned relative to one another, and average the shifted normalized plurality of calibration output signals so as to generate a single shifted normalized calibration output signal. In this example, the single shifted normalized calibration output signal may comprise the expected output signal. In this example, each of the plurality of calibration output signals may indicate the relative proximity of magnetic target 210 to the corresponding one of magnetic field sensors 216A-216G as magnetic target 210 passes the corresponding one of magnetic field sensors 216A-216G.

In other examples, to generate the expected output signal, position sensor 200 and/or the other component of the system may be configured to generate the expected output signal based at least in part on a model of one or more of enclosure 204, object 208, magnetic field sensors 216A-216G, magnetic target 210, and relative positions thereof.

In some examples, to generate the expected output signal, position sensor 200 and/or the other component of the system may be configured to periodically generate the expected output signal.

Additionally, position sensor 200 and/or the other component of the system may be further configured to receive a plurality of actual output signals from magnetic field sensors 216A-216G, wherein each of the plurality of actual output signals indicates a relative proximity of magnetic target 210 coupled to object 208 to the corresponding one of magnetic field sensors 216A-216G.

In this example, position sensor 200 and/or the other component of the system may be still further configured to superimpose the expected output signal over the plurality of actual output signals, and iteratively shift the expected output signal over position relative to the plurality of actual output signals and compare the shifted expected output signal to the plurality of actual output signals, until the shifted expected output signal compared to the plurality of actual output signals corresponds to a substantially minimized error parameter.

For example, the substantially minimized error parameter may comprise a substantially minimized Least Squares (LS) error parameter, such that, e.g., the substantially minimized LS error parameter may correspond to a substantially minimized sum of squared differences among the shifted expected output signal and the plurality of actual output signals.

In another example, the substantially minimized error parameter may comprise a second substantially minimized Least Squares error parameter that uses the output of an initial substantially minimized Least Squares calculation as input for computing a second substantially minimized least squares function. Computing the second substantially minimized Least Squares error parameter may include a substantially minimized LS error parameter that is a result of using an output of an initial substantially minimized Least Squares error calculation as input to a second substantially minimized least squares calculation. Executing a second substantially minimized Least Squares error calculation may provide additional accuracy or measure position of a magnetic target to a different granularity level in some examples. The second substantially minimized Least Squares error calculation may more accurately correspond to a substantially minimized sum of squared differences among the shifted expected output signal and the plurality of actual output signals, in some examples. For example, in some implementations, a magnetic position sensor may detect a position of a magnetic target to an accuracy in a range of 5 to 0.5 millimeters after an initial least squares error calculation, and improve the accuracy to within a range of 1.0 to 0.01 millimeter after a second substantially minimized Least Squares error parameter calculation. A calculation process may provide a substantially minimized Least Squares calculation in that a result may provide a calculation in which the least squares are minimized as much as or nearly as much as may be feasible with a particular set of hardware or within acceptable or nominal error tolerance for a particular application, for example.

Finally, position sensor 200 and/or the other component of the system may be configured to determine the position of object 208 within enclosure 204 over the position range based at least in part on the shifted expected output signal. In some examples, position sensor 200 and/or the other component of the system may also be configured to output one or more signals indicative of the determined position of object 208 located within enclosure 204 over the position range, e.g., for subsequent processing and/or storage.

In the examples described above, the position range may comprise a substantially linear position range, a substantially angular position range, or any combination thereof. Furthermore, as previously described, magnetic target 210 may comprise one or more first magnetic poles and one or more second magnetic poles disposed on opposite ends of magnetic target 210 so as to generate uniform magnetic field 212. Moreover, as also previously described, enclosure 204 may comprise an enclosure that is configured to attenuate a magnetic field (e.g., uniform magnetic field 212) passing through the enclosure. For example, as explained above, enclosure 204 may comprise hydraulic cylinder 202, such that object 208 comprises a portion of piston 206 disposed within hydraulic cylinder 202. Finally, as also previously described, one or more of magnetic field sensors 216A-216G may comprise one or more magnetoresistive sensors, which may include, e.g., MR and AMR sensors.

In this manner, position sensor 200 of FIG. 2A represents an example of a position sensor included within a position sensor calibration system configured to perform a method of sensing a position of an object located within an enclosure over a position range, wherein the method performed by the position sensor calibration system comprises generating an expected output signal of each of a plurality of magnetic field sensors disposed along an outer surface of the enclosure between a first end and a second end of the enclosure, receiving a plurality of actual output signals from the plurality of magnetic field sensors, wherein each of the plurality of actual output signals indicates a relative proximity of a magnetic target coupled to the object to the corresponding one of the plurality of magnetic field sensors, superimposing the expected output signal over the plurality of actual output signals, iteratively shifting the expected output signal over position relative to the plurality of actual output signals and comparing the shifted expected output signal to the plurality of actual output signals, until the shifted expected output signal compared to the plurality of actual output signals corresponds to a substantially minimized error parameter, and determining the position of the object within the enclosure over the position range based at least in part on the shifted expected output signal.

Figure 2B:
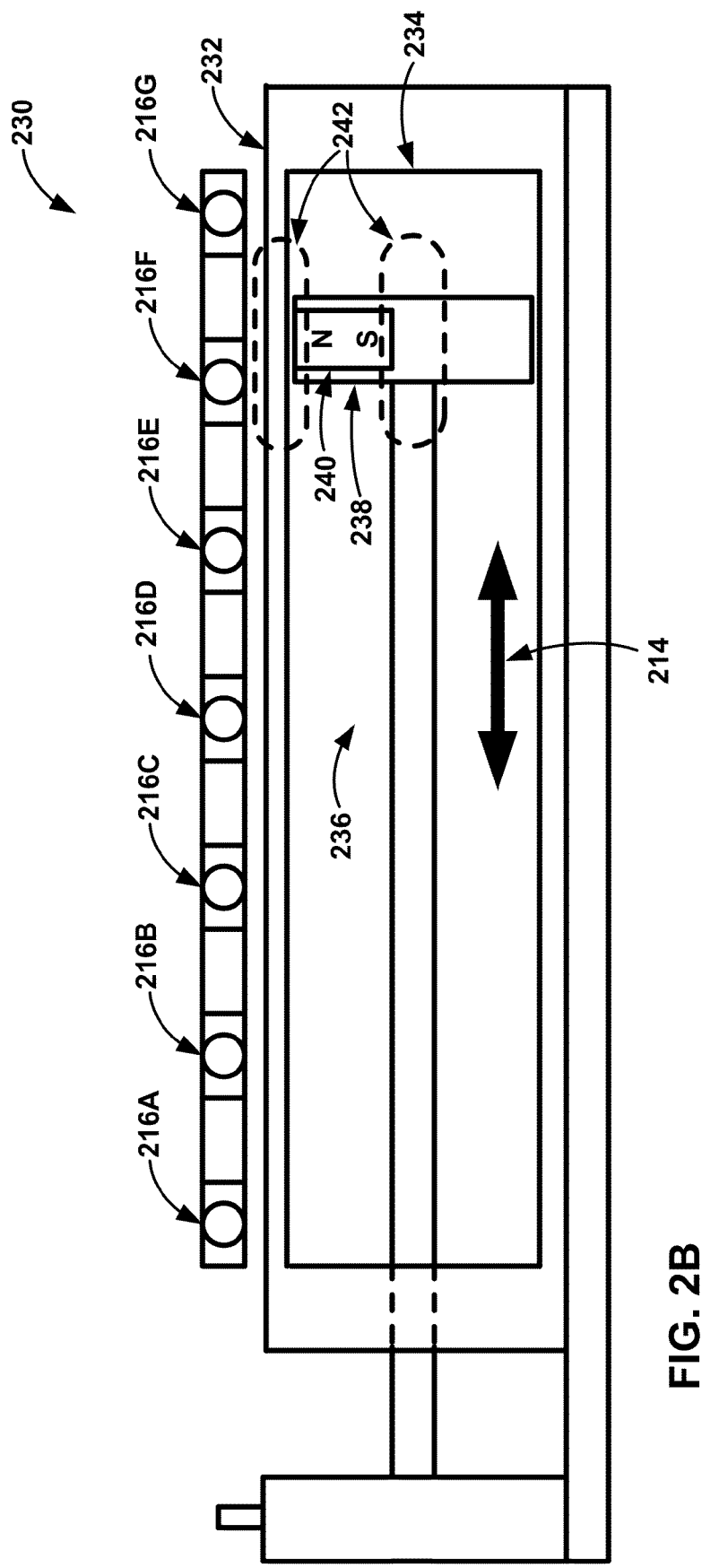

FIG. 2B is a conceptual diagram of another example of a linear position sensor 230 that may be used in conjunction with the example position sensor calibration system of FIG. 1, consistent with the techniques of this disclosure. The example linear position sensor 230 of FIG. 2B is similar in many respects to the example linear position sensor 200 of FIG. 2A, with like numbering for components in common, but linear position sensor 230 includes a magnetic target 240 embedded inside piston 236. In particular, linear position sensor 230 includes magnetic target 240 inside a portion of piston 236 referred to herein as object 238. Thus, whereas magnetic object 208 is positioned adjacent to a shaft of movable piston 206 in the example of FIG. 2A, object 238 is positioned within movable piston 236 in the example of FIG. 2B.

Magnetic target 240 may be embedded in piston 236 such that one surface of magnetic target 240 may be positioned flush with a surface of object 238, facing the side wall of enclosure 234, and facing in the direction of magnetic field sensors 216A-216G, as in the example depicted in FIG. 2B. As shown in the example of FIG. 2B, magnetic target 240 is oriented with the south to north magnetic axis aligned outward in the direction of magnetic field sensors 216A-216G. Magnetic target 240 may also be positioned within piston 236 in different orientations in other examples, such as with a north to south magnetic axis aligned outward in the direction of magnetic field sensors 216A-216G.

As shown in the example of FIG. 2B, position sensor 230 is implemented as part of a hydraulic cylinder 232 (a cross-sectional view of which is provided in FIG. 2B), which includes, in part, an enclosure 234, a movable piston 236 disposed within enclosure 234 so as to move in a direction 214 (i.e., a left-to-right direction with reference to hydraulic cylinder 232), and a portion of piston 236, which, in this example, may be referred to as the object 238. In the example of FIG. 2B, position sensor 230 may be configured to sense a position of object 238 located within enclosure 234 over a position range. For example, the position range may be defined by the dimensions of enclosure 234, e.g., by a first end and a second end of enclosure 234. In some examples, the position range may be defined by the inner dimensions of enclosure 234. In various examples, in a similar manner as previously described, enclosure 234 of hydraulic cylinder 232 may comprise a metallic enclosure, or an enclosure made of another material, such that enclosure 234 attenuates magnetic fields passing through enclosure 234.

In some examples, the magnetic field sensors 216A-216G may also be pre-biased to the magnetic orientation of magnetic target 210 or 240, and optimized to be sensitive to the magnetic orientation of magnetic target 210 or 240. For example, with magnetic target 210 or 240 oriented with south to north magnetic axis aligned outward in the direction of magnetic field sensors 216A-216G, as in the examples of FIGS. 2 and 2B, magnetic field sensors 216A-216G may be calibrated to be sensitive to the south to north magnetic axis of magnetic target 210/240 aligned outward in the direction of magnetic field sensors 216A-216G. Magnetic field sensors 216A-216G may be calibrated for the orientation of a magnetic target either during initial manufacture and assembly in a factory, or afterward in a field installation, in different examples. Magnetic field sensors 216A-216G may also be initially positioned to be sensitive to a certain magnetic axis orientation of a magnetic target 210/240, and be subsequently calibrated to optimize their sensitivity to a particular magnetic target 210/240.

Figure 3A:
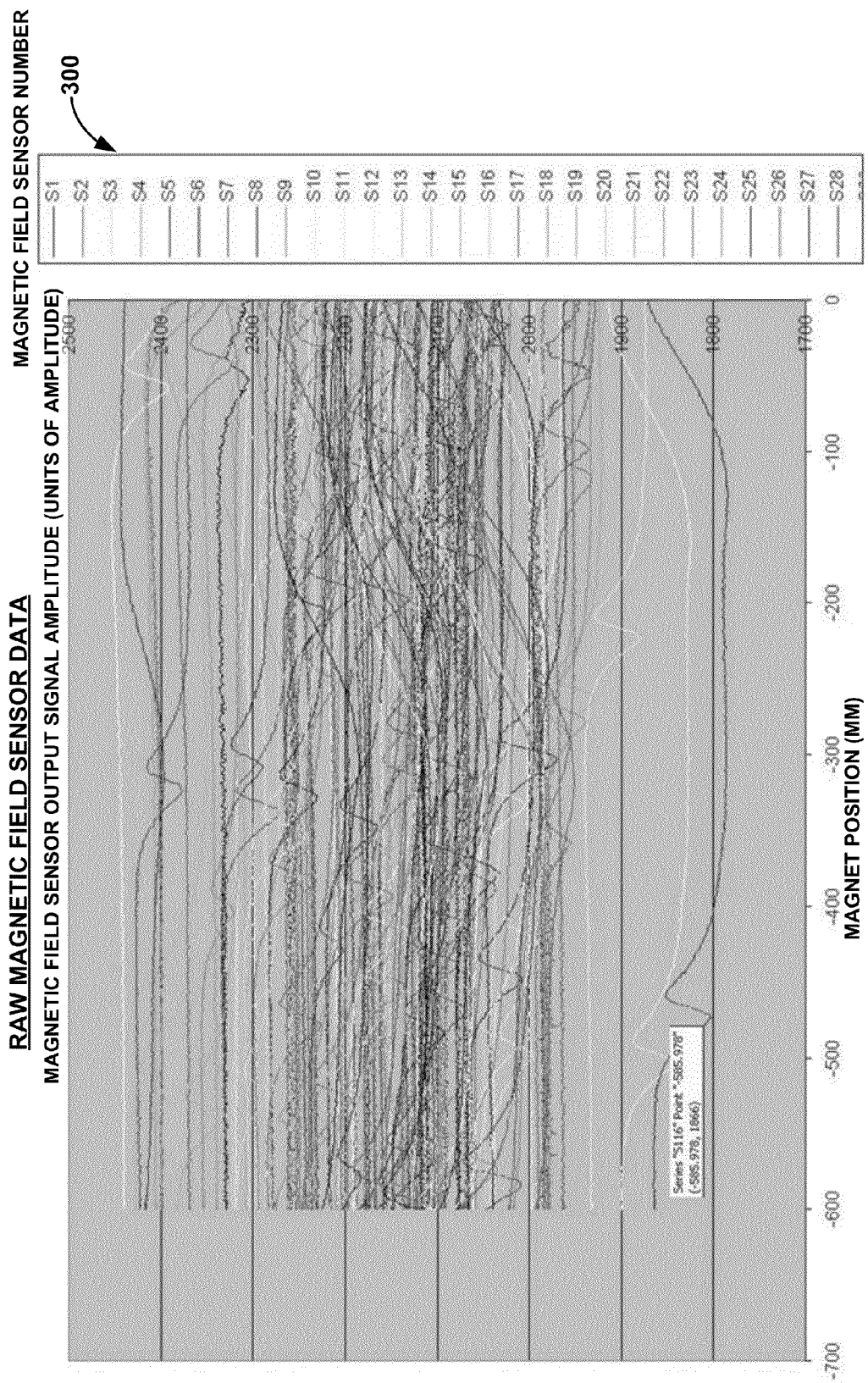
FIGS. 3A-3D are graphs that illustrate examples of output signals of a plurality of magnetic field sensors of a linear position sensor, consistent with the techniques of this disclosure.

FIGS. 3A-3D are graphs that illustrate examples of output signals of a plurality of magnetic field sensors of a linear position sensor, consistent with the techniques of this disclosure. For example, FIG. 3A illustrates an example of a plurality of output signals 300 received from a plurality of magnetic field sensors (e.g., magnetic field sensors 216A-216G of FIGS. 2A and 2B) of a position sensor (e.g., position sensor 108 of FIG. 1, or position sensors 200 or 230 of FIGS. 2A or 2B). In this example, each of output signals 300 may indicate a relative proximity of a magnetic target (e.g., magnetic targets 210 or 240 of FIGS. 2A or 2B) coupled to an object (e.g., objects 208, 238 of FIGS. 2A or 2B) to the corresponding one of the plurality of magnetic field sensors. As such, output signals 300 of FIG. 3A may be referred to as "raw sensor data."

As shown in FIG. 3A, each of output signals 300 is represented using an amplitude scale and a position scale, wherein the amplitude scale comprises a range of 1700 to 2500 units of amplitude (e.g., millivolts (mV), Volts (V), or any scaled versions thereof), and the position scale comprises a range of 0 to −700 mm. As also shown in FIG. 3A, output signals 300 each have a substantially similar characteristic, which, for each of output signals 300, occurs within a unique subset of the range of 1700 to 2500 units of amplitude, and over a unique subset of the range of 0 to −700 mm.

Figure 3B:
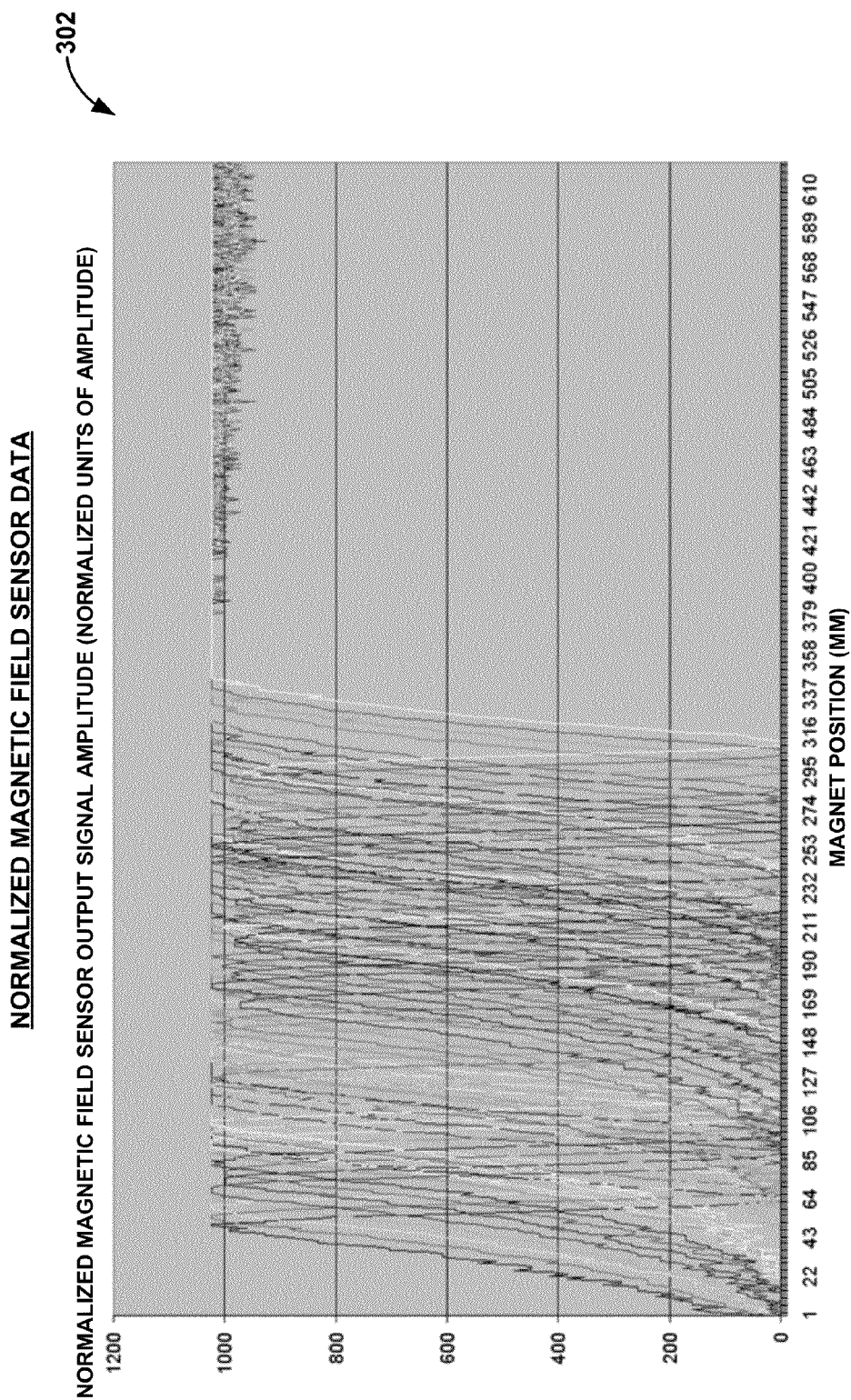

Similarly, FIG. 3B illustrates an example of output signals 300 that have been normalized such that each of normalized output signals 302 comprises a substantially same dynamic range. As shown in FIG. 3B, each of normalized output signals 302 is represented using an amplitude scale and a position scale, wherein the amplitude scale comprises a range of 0 to 1200 normalized units of amplitude (e.g., normalized millivolts (mV), Volts (V), or any normalized scaled versions thereof), and the position scale comprises a range of 0 to 610 mm. In other words, to produce normalized output signals 302, output signals 300 may be scaled and aligned over amplitude so as to comprise the substantially same dynamic range. In the example of FIG. 3B, only a portion of output signals 300 that have been normalized in the manner described above is shown.

Figure 3C:
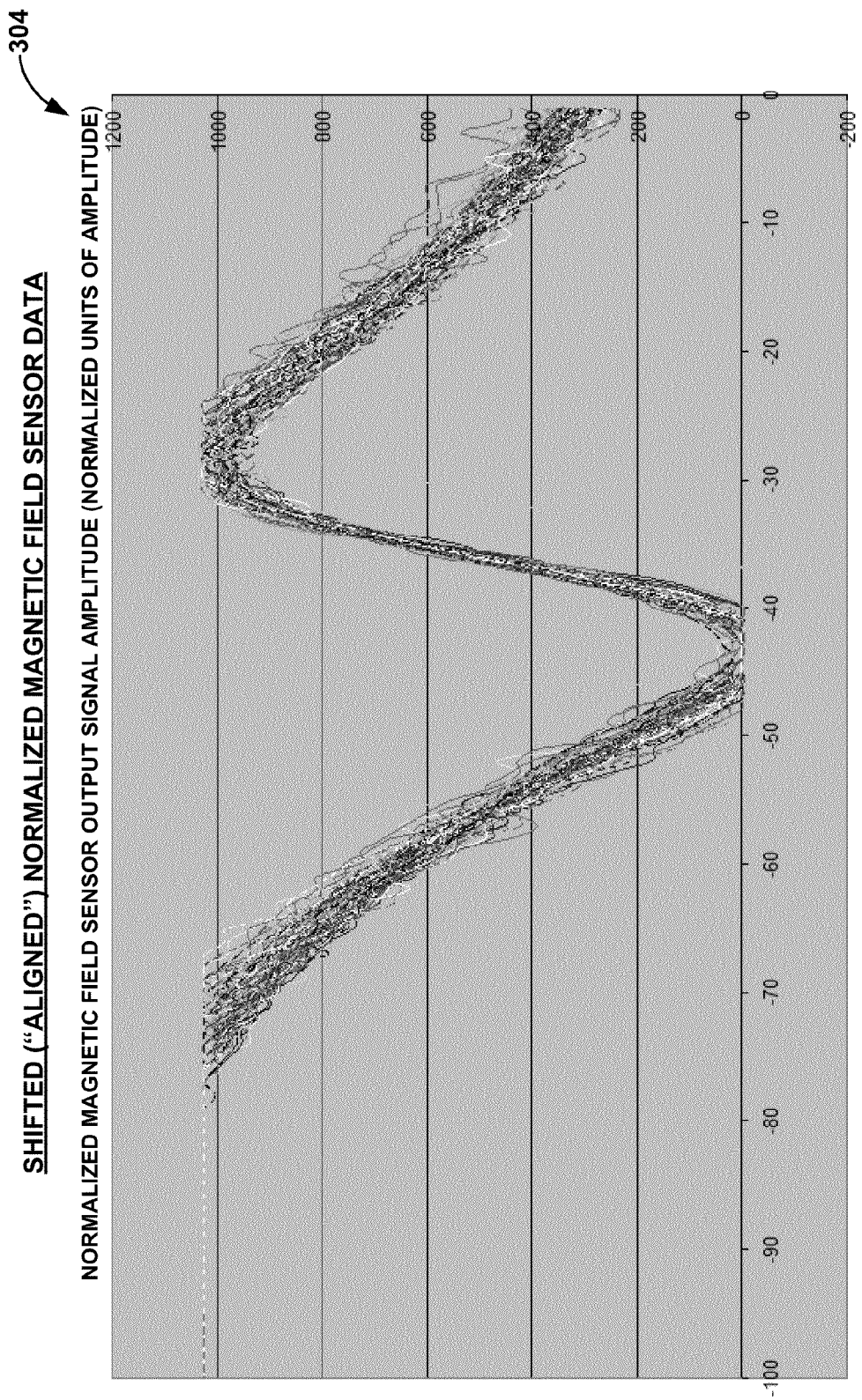

Furthermore, FIG. 3C illustrates an example of normalized output signals 302 that have been shifted over position such that the signals of normalized output signals 304 are substantially aligned relative to one another. As shown in FIG. 3C, each of shifted normalized output signals 304 is represented using an amplitude scale and a position scale, wherein the amplitude scale comprises the range of 0 to 1200 normalized units of amplitude previously described, and the position scale comprises a "shifted" range of 0 to 100 mm. In this example, the range of 0 to 100 mm corresponds to a subset of the previously described range of range of 0 to 610 mm that corresponds to each of normalized output signals 302 prior to having been shifted. In other words, to produce shifted normalized output signals 304, normalized output signals 302 may be shifted and aligned over position so as to be substantially aligned relative to one another, while still spanning their original position range. In the example of FIG. 3C, only a portion of output signals 302 that have been shifted in the manner described above is shown.

Figure 3D:
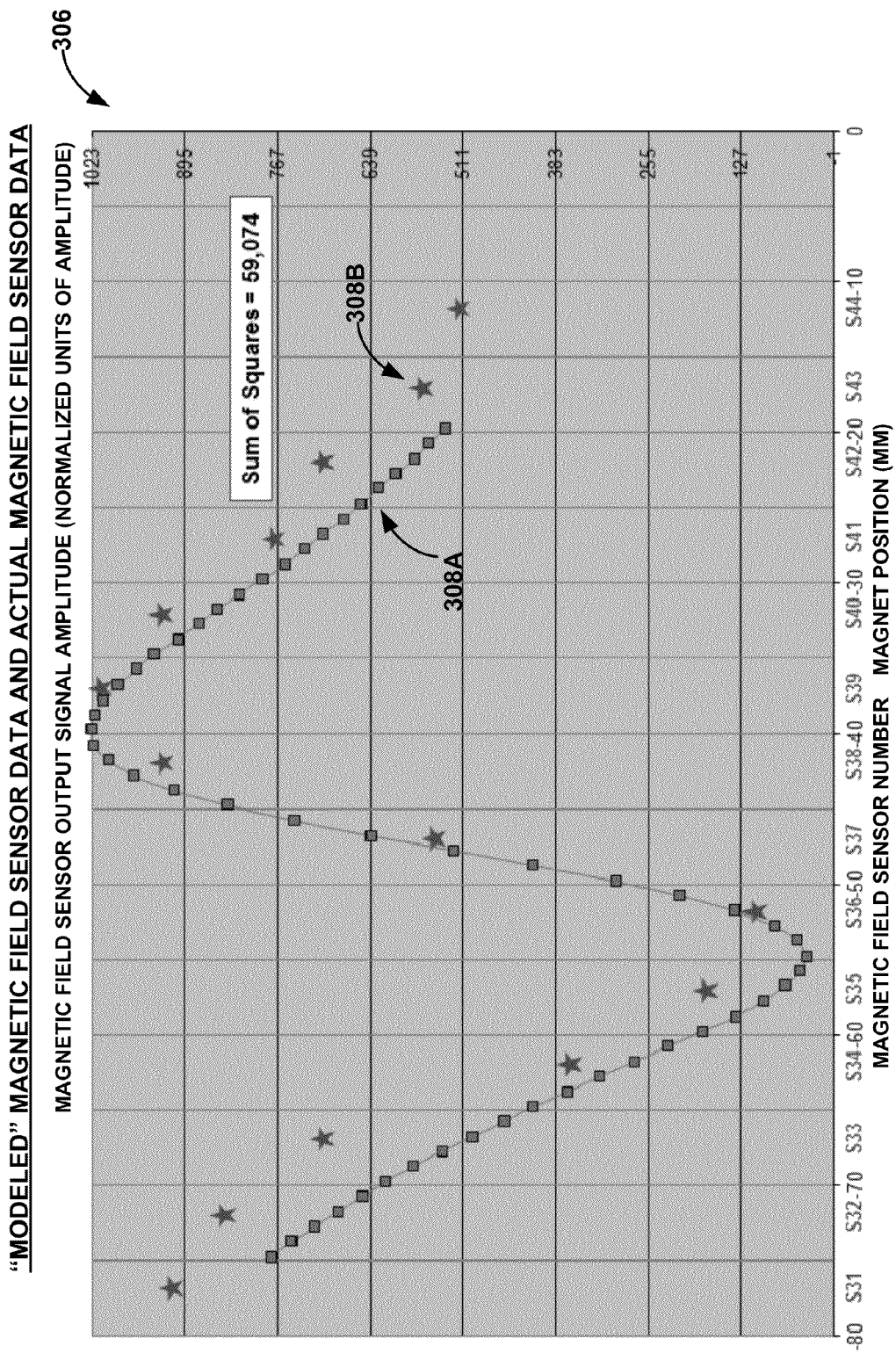

Finally, FIG. 3D illustrates an example of averaging shifted normalized output signals 304 previously described so as to generate a single shifted normalized output signal 306. As explained above, the single shifted normalized output signal 306 may comprise an expected output signal 308A, which may be used in accordance with the techniques of this disclosure to calibrate the linear position sensor. For example, expected output signal 308A may comprise an average of shifted normalized output signals 304 of FIG. 3C. Alternatively, as also previously explained, expected output signal 308A may be generated based at least in part on a model of one or more of the enclosure, the object, the plurality of magnetic field sensors, the magnetic target, and relative positions thereof.

In accordance with various examples, FIG. 3D further illustrates superimposing the expected output signal 308A (e.g., whether generated using the techniques described above with reference to FIGS. 3A-3C, or modeled in the manner also previously described) over actual output signals 308B. Each of actual output signals 308B may comprise output signals of one or more of the plurality of magnetic field sensors, and may indicate a relative proximity of the magnetic target coupled to the object to the corresponding one of the one or more of the plurality of magnetic field sensors. In the example of FIG. 3D, expected output signal 308A may be iteratively shifted (e.g., shifted to the left or the right) over position relative to actual output signals 308B and compared to actual output signals 308B, until the shifted expected output signal 308A compared to actual output signals 308B corresponds to a substantially minimized error parameter, consistent with the techniques disclosed herein. In the example of FIG. 3D, the depicted iteration of the above-described iterative process results an error parameter equal to 59,074, as one example.

Figure 4:
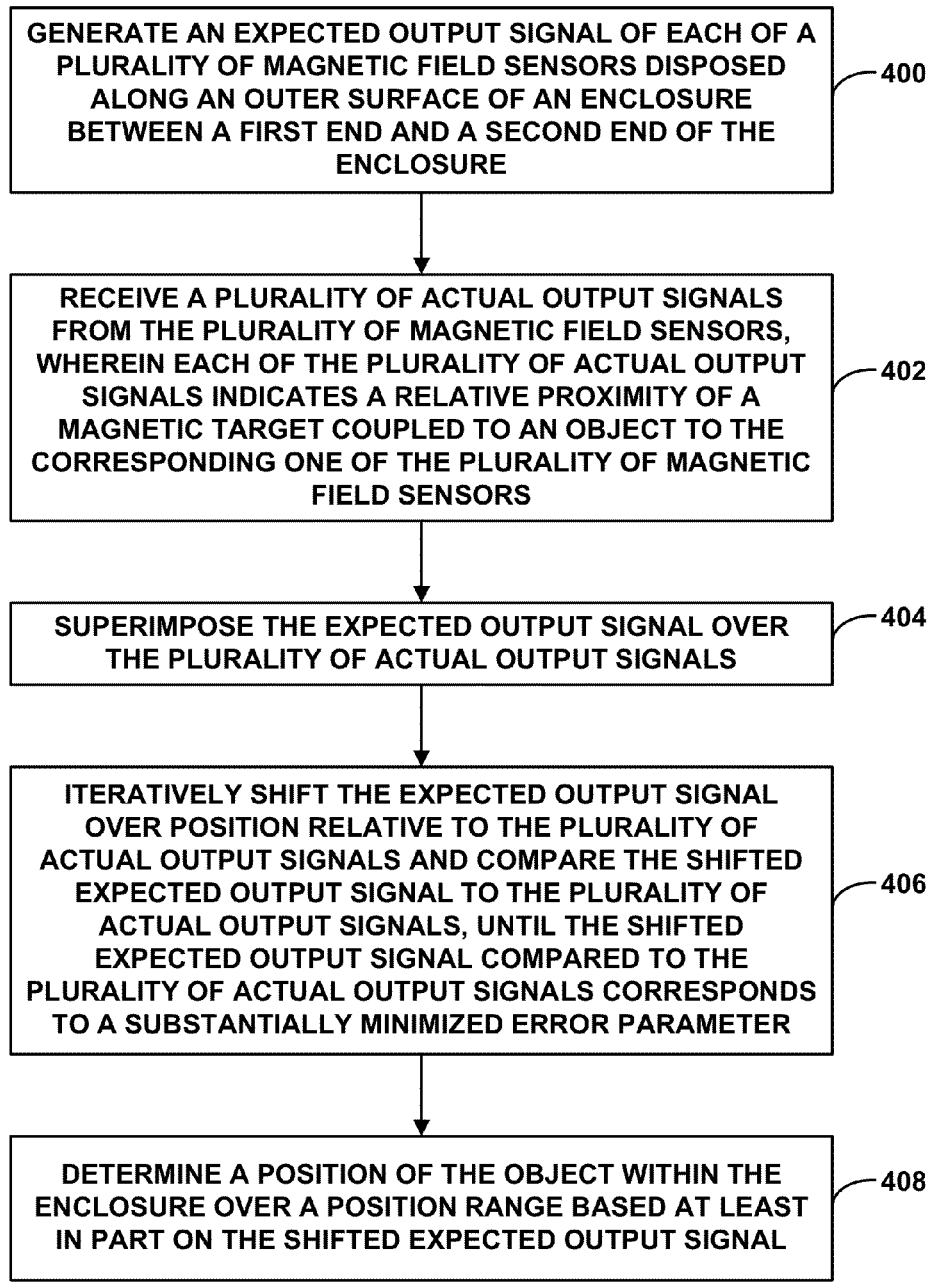
FIG. 4 is a flow diagram that illustrates one example of a method of calibrating a position sensor, consistent with the techniques of this disclosure.

FIG. 4 is a flow diagram that illustrates one example of a method of calibrating a position sensor, consistent with the techniques of this disclosure. The techniques of FIG. 4 may generally be performed by any processing unit or processor, whether implemented in hardware, software, firmware, or a combination thereof, and when implemented in software or firmware, corresponding hardware may be provided to execute instructions for the software or firmware. For purposes of example, the techniques of FIG. 4 are described with respect to position sensor calibration system 100 (FIG. 1), position sensor 108 (FIGS. 1) and 200, 230 (FIGS. 2A and 2B), and processing module 112 (FIG. 1), as well as various components thereof, although it should be understood that other systems or devices may be configured to perform similar techniques. Moreover, the steps illustrated in FIG. 4 may be performed in a different order or in parallel, and additional steps may be added and certain steps omitted, without departing from the techniques of this disclosure.

In one example, one or more of a position sensor (e.g., 108, 200) and a processing module (e.g., 112) of a position sensor calibration system (e.g., 100) that includes the position sensor and/or the processing module may be configured to sense a position of an object (e.g., 208) located within an enclosure (e.g., 204) over a position range. For example, the one or more of the position sensor and the processing module may initially generate an expected output signal of each of a plurality of magnetic field sensors (e.g., 216A-216G) disposed along an outer surface of the enclosure between a first end and a second end of the enclosure (400).

In some examples, to generate the expected output signal, the one or more of the position sensor and the processing module may receive a plurality of calibration output signals (e.g., 300) from the plurality of magnetic field sensors, wherein each of the plurality of calibration output signals indicates a relative proximity of the magnetic target to the corresponding one of the plurality of magnetic field sensors. The one or more of the position sensor and the processing module may further normalize the plurality of calibration output signals (e.g., 302) such that each of the plurality of calibration output signals comprises a substantially same dynamic range. The one or more of the position sensor and the processing module may also shift the normalized plurality of calibration output signals over position such that the signals of the normalized plurality of calibration output signals are substantially aligned relative to one another (e.g., 304). Finally, the one or more of the position sensor and the processing module may average the shifted normalized plurality of calibration output signals so as to generate a single shifted normalized calibration output signal (e.g., 308A), wherein the single shifted normalized calibration output signal comprises the expected output signal.

In other examples, to generate the expected output signal, the one or more of the position sensor and the processing module may generate the expected output signal based at least in part on a model of one or more of the enclosure, the object, the plurality of magnetic field sensors, the magnetic target, and relative positions thereof.

In various examples, the one or more of the position sensor and the processing module may further receive a plurality of actual output signals (e.g., 308B) from the plurality of magnetic field sensors, wherein each of the plurality of actual output signals indicates a relative proximity of a magnetic target (e.g., 210) coupled to the object to the corresponding one of the plurality of magnetic field sensors (402).

The one or more of the position sensor and the processing module may still further superimpose the expected output signal over the plurality of actual output signals (404) (e.g., 308B), and iteratively shift the expected output signal over position relative to the plurality of actual output signals and compare the shifted expected output signal to the plurality of actual output signals, until the shifted expected output signal compared to the plurality of actual output signals corresponds to a substantially minimized error parameter (406).

Finally, the one or more of the position sensor and the processing module may determine the position of the object within the enclosure over the position range based at least in part on the shifted expected output signal (408).

In some examples, the one or more of the position sensor and the processing module may also output one or more signals (e.g., 114) indicative of the determined position of the object within the enclosure over the position range. For example, the one or more of the position sensor and the processing module may output the one or more output signals for subsequent processing and/or storage within one or more memories, or memory devices, as described above with reference to system 100 of FIG. 1.

In this manner, the method of FIG. 4 represents an example of a method of sensing a position of an object located within an enclosure over a position range, the method comprising generating an expected output signal of each of a plurality of magnetic field sensors disposed along an outer surface of the enclosure between a first end and a second end of the enclosure, receiving a plurality of actual output signals from the plurality of magnetic field sensors, wherein each of the plurality of actual output signals indicates a relative proximity of a magnetic target coupled to the object to the corresponding one of the plurality of magnetic field sensors, superimposing the expected output signal over the plurality of actual output signals, iteratively shifting the expected output signal over position relative to the plurality of actual output signals and comparing the shifted expected output signal to the plurality of actual output signals, until the shifted expected output signal compared to the plurality of actual output signals corresponds to a substantially minimized error parameter, and determining the position of the object within the enclosure over the position range based at least in part on the shifted expected output signal.

This disclosure also includes an attached appendix, which forms part of this disclosure and is expressly incorporated herein. The attached appendix provides additional details and examples of the techniques and devices described herein.

The techniques of this disclosure may be implemented in a wide variety of computer devices. Any components, units, or modules that have been described are provided to emphasize functional aspects, and do not necessarily require realization by different hardware units. The techniques described herein may also be implemented in hardware, software, firmware, or any combination thereof Any features described as modules, units, or components may be implemented together in an integrated logic device, or separately as discrete but interoperable logic devices. In some cases, various features may be implemented as an integrated circuit device, such as an integrated circuit chip, or chipset.

If any aspect of the techniques are implemented in software, the techniques may be realized at least in part by a computer-readable storage medium comprising instructions that, when executed in a processor, performs one or more of the methods described above. The computer-readable storage medium may comprise a tangible computer-readable storage medium, and may form part of a larger product. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disc (CD), digital versatile disc (DVD), Blu-ray disc, holographic data storage media, or other non-volatile storage device.

The memory, or memory devices, described herein, which may be used as part of the described techniques, may also be realized in any of a wide variety of memory, or memory devices, including but not limited to, RAM, SDRAM, NVRAM, EEPROM, FLASH memory, dynamic RAM (DRAM), magnetic RAM (MRAM), or other types of memory.

The term "processor" as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

Various examples have been described. These and other examples are within the scope of the following claims.

What is claimed is:

1. A method of sensing a position of an object located within an enclosure over a position range, the method comprising:
   generating an expected output signal of each of a plurality of magnetic field sensors disposed along an outer surface of the enclosure between a first end and a second end of the enclosure;
   receiving a plurality of actual output signals from the plurality of magnetic field sensors, wherein each of the plurality of actual output signals indicates a relative proximity of a magnetic target coupled to the object to the corresponding one of the plurality of magnetic field sensors;
   superimposing the expected output signal over the plurality of actual output signals;
   iteratively shifting the expected output signal of each of the plurality of magnetic field sensors over position relative to the actual output signals of each of the plurality of magnetic field sensors and comparing the shifted expected output signal to the plurality of actual output signals, until the shifted expected output signal compared to the plurality of actual output signals corresponds to a substantially minimized error parameter; and determining the position of the object within the enclosure over the position range based at least in part on the shifted expected output signal.

2. The method of claim 1, wherein the expected output signal comprises a signal that is expected to be output by each of the plurality of magnetic field sensors as the magnetic target passes the respective one of the plurality of magnetic field sensors.

3. The method of claim 1, wherein generating the expected output signal comprises:

receiving a plurality of calibration output signals from the plurality of magnetic field sensors, wherein each of the plurality of calibration output signals indicates a relative proximity of the magnetic target to the corresponding one of the plurality of magnetic field sensors;

normalizing the plurality of calibration output signals such that each of the plurality of calibration output signals comprises a substantially same dynamic range;

shifting the normalized plurality of calibration output signals over position such that the signals of the normalized plurality of calibration output signals are substantially aligned relative to one another; and averaging the shifted normalized plurality of calibration output signals so as to generate a single shifted normalized calibration output signal, wherein the single shifted normalized calibration output signal comprises the expected output signal.

4. The method of claim 3, wherein each of the plurality of calibration output signals indicates the relative proximity of the magnetic target to the corresponding one of the plurality of magnetic field sensors as the magnetic target passes the corresponding one of the plurality of magnetic field sensors.

5. The method of claim 1, wherein generating the expected output signal comprises generating the expected output signal based at least in part on a model of one or more of the enclosure, the object, the plurality of magnetic field sensors, the magnetic target, and relative positions thereof.

6. The method of claim 1, wherein generating the expected output signal comprises periodically generating the expected output signal.

7. The method of claim 1, wherein the position range comprises a substantially linear position range.

8. The method of claim 1, wherein the position range comprises a substantially angular position range.

9. The method of claim 1, wherein the magnetic target comprises one or more first magnetic poles and one or more second magnetic poles disposed on opposite ends of the magnetic target so as to generate a uniform magnetic field.

10. The method of claim 1, wherein the enclosure comprises an enclosure that is configured to attenuate a magnetic field passing through the enclosure.

11. The method of claim 10, wherein the enclosure comprises a hydraulic cylinder, and wherein the object comprises a portion of a movable piston disposed within the hydraulic cylinder.

12. The method of claim 11, wherein the object is positioned adjacent to a shaft of the movable piston.

13. The method of claim 11, wherein the object is positioned within the movable piston.

14. The method of claim 1, wherein the substantially minimized error parameter comprises a substantially minimized Least Squares (LS) error parameter, and wherein the substantially minimized LS error parameter corresponds to a substantially minimized sum of squared differences among the shifted expected output signal and the plurality of actual output signals.

15. The method of claim 14, wherein the substantially minimized error parameter further comprises a second substantially minimized Least Squares (LS) error parameter, and wherein the substantially minimized LS error parameter is a result of using an output of an initial substantially minimized Least Squares error calculation as input to a second substantially minimized Least Squares calculation.

16. The method of claim 1, wherein one or more of the plurality of magnetic field sensors comprise one or more magnetoresistive sensors.

17. A device for sensing a position of an object located within an enclosure over a position range, the device comprising:

means for generating an expected output signal of each of a plurality of magnetic field sensors disposed along an outer surface of the enclosure between a first end and a second end of the enclosure;

means for receiving a plurality of actual output signals from the plurality of magnetic field sensors, wherein each of the plurality of actual output signals indicates a relative proximity of a magnetic target coupled to the object to the corresponding one of the plurality of magnetic field sensors;

means for superimposing the expected output signal over the plurality of actual output signals;

means for iteratively shifting the expected output signal of each of the plurality of magnetic field sensors over position relative to the actual output signals of each of the plurality of magnetic field sensors and comparing the shifted expected output signal to the plurality of actual output signals, until the shifted expected output signal compared to the plurality of actual output signals corresponds to a substantially minimized error parameter; and means for determining the position of the object within the enclosure over the position range based at least in part on the shifted expected output signal.

18. The device of claim 17, wherein the expected output signal comprises a signal that is expected to be output by each of the plurality of magnetic field sensors as the magnetic target passes the respective one of the plurality of magnetic field sensors.

19. The device of claim 17, wherein the means for generating the expected output signal comprises:

means for receiving a plurality of calibration output signals from the plurality of magnetic field sensors, wherein each of the plurality of calibration output signals indicates a relative proximity of the magnetic target to the corresponding one of the plurality of magnetic field sensors;

means for normalizing the plurality of calibration output signals such that each of the plurality of calibration output signals comprises a substantially same dynamic range;

means for shifting the normalized plurality of calibration output signals over position such that the signals of the normalized plurality of calibration output signals are substantially aligned relative to one another; and means for averaging the shifted normalized plurality of calibration output signals so as to generate a single shifted normalized calibration output signal, wherein the single shifted normalized calibration output signal comprises the expected output signal.

20. An apparatus for sensing a position of an object located within an enclosure over a position range, the apparatus being configured to:
- generate an expected output signal of each of a plurality of magnetic field sensors disposed along an outer surface of the enclosure between a first end and a second end of the enclosure;
- receive a plurality of actual output signals from the plurality of magnetic field sensors, wherein each of the plurality of actual output signals indicates a relative proximity of a magnetic target coupled to the object to the corresponding one of the plurality of magnetic field sensors;
- superimpose the expected output signal over the plurality of actual output signals;
- iteratively shift the expected output signal of each of the plurality of magnetic field sensors over position relative to the actual output signals of each of the plurality of magnetic field sensors and comparing the shifted expected output signal to the plurality of actual output signals, until the shifted expected output signal compared to the plurality of actual output signals corresponds to a substantially minimized error parameter; and
- determine the position of the object within the enclosure over the position range based at least in part on the shifted expected output signal.

* * * * *